United States Patent [19]

Ramachandran et al.

[11] Patent Number: 5,466,837
[45] Date of Patent: Nov. 14, 1995

[54] PROCESS FOR THE PRODUCTION OF HYDROCARBON PARTIAL OXIDATION PRODUCTS

[75] Inventors: Ramakrishnan Ramachandran, Allendale; Loc H. Dao, Bound Brook, both of N.J.

[73] Assignee: The BOC Group, Inc., New Providence, N.J.

[21] Appl. No.: 232,544

[22] Filed: Apr. 22, 1994

Related U.S. Application Data

[63] Continuation-in-part of Ser. No. 129,911, Sep. 30, 1993, abandoned.

[51] Int. Cl.[6] .................... C07C 253/26; C07C 47/22; C07C 17/08; C07D 301/10
[52] U.S. Cl. .................... 549/533; 549/534; 549/535; 558/319; 558/320; 558/324; 558/325; 558/326; 568/479; 570/248; 570/250; 562/512.2; 562/545; 560/241.1; 560/243
[58] Field of Search .................... 558/319, 320, 558/326, 324, 325; 549/533, 534, 535; 568/479; 570/248, 250; 562/512.2, 545; 560/241.1, 243

[56] References Cited

U.S. PATENT DOCUMENTS

| | | | |
|---|---|---|---|
| 4,849,538 | 7/1989 | Ramachandran et al. | 558/319 |
| 4,868,330 | 9/1989 | Ramachandran et al. | 558/319 X |
| 4,870,201 | 9/1989 | Ramachandran et al. | 558/319 |
| 4,917,711 | 4/1990 | Xie et al. | 55/68 |
| 4,943,650 | 7/1990 | Ramachandran et al. | 558/319 |
| 5,015,756 | 5/1991 | Ramachandran et al. | 558/320 |
| 5,179,215 | 1/1993 | Ramachandran et al. | |
| 5,262,547 | 11/1993 | Ramachandran et al. | |
| 5,264,608 | 11/1993 | Ramachandran et al. | 558/319 |
| 5,268,497 | 12/1993 | Ramachandran et al. | 558/320 |
| 5,278,319 | 1/1994 | Ramachandran et al. | |

FOREIGN PATENT DOCUMENTS 221128  5/1980  Germany.

OTHER PUBLICATIONS

Adsorptive Separation of Propylene—Propane Mixtures—Harri Jarvelin and James R. Fair pp. 2201–2207; Ind. Eng. Chem. Res., 32 (1993).
Zeolite Molecular Sieves—Donald W. Breck,—Union Carbide Corporation, (1974) pp. 635, 637, 641–642.
Union Carbide Molecular Sieves Hydrocarbon Materials Data Sheets (Propylene Adsorption, Hydrocarbon Adsorption, Propane Adsorption, Ethylene Adsorption, Ethane Adsorption, Vapor Adsorbate Equilibira Data, Capacity for Ethane–Ethylene Mixtures); Isotherm Data Sheet No. 151, Isotherm Data Sheet No. 71, Isotherm Data Sheet No. 74, Isotherm Data Sheet No. 141, Isotherm Data Sheet No. 121, Isotherm Data Sheet No. 101, Isotherm data Sheet No. 131, Isotherm Data Sheet No. 132.

*Primary Examiner*—Joseph Paul Brust
*Attorney, Agent, or Firm*—Coleman R. Reap; Larry R. Cassett

[57] ABSTRACT

An ethylene stream which contains ethane as an impurity or a propylene stream which contains propane as an impurity is subjected to adsorption at a temperature of 50° to 200° C. in a bed of adsorbent which selectively adsorbs ethylene or propylene, thereby adsorbing substantially all of the ethylene or propylene. The purified ethylene or propylene stream is then subjected to partial oxidation in the presence of oxygen and, optionally ammonia to produce various partial oxidation products. The process is operated on a low per pass conversion with recycle of unreacted ethylene or propylene. In the system of the invention the adsorption unit may be upstream or downstream of the partial oxidation reactor.

41 Claims, 2 Drawing Sheets

PROCESS FOR THE PRODUCTION OF HYDROCARBON PARTIAL OXIDATION PRODUCTS

RELATED CASE

This application is a continuation-in-part of application Ser. No. 129,911, filed Sep. 30, 1993, now abandoned.

FIELD OF THE INVENTION

The present invention is directed to a process for producing partial oxidation products by the reaction of ethylene or propylene and an oxygen-containing gas in the presence of a suitable catalyst, and more particularly to a vapor phase process in which a hydrocarbon partial oxidation product is produced by contacting an ethylene stream or a propylene stream containing propane as an impurity with an oxygen-containing gas in the presence of an appropriate oxidation catalyst.

BACKGROUND OF THE INVENTION

Certain partial oxidation products are produced commercially by the oxidation of ethylene or propylene in the vapor phase over a suitable catalyst. For example, ethylene oxide and vinyl chloride are produced by the partial oxidation of ethylene with oxygen in the presence of selected catalysts, and acrylonitrile, propylene oxide and acrolein are produced by the partial oxidation of propylene with oxygen in the presence of selected catalysts. Air is generally used as the source of oxygen, because of its low cost and ready availability. The reaction can be carried out in any suitable reactor and it produces the desired partial oxidation product and generally carbon monoxide, carbon dioxide and water as byproducts. The reaction conversion is usually less than 100%; accordingly the reactor effluent also generally contains unreacted ethylene or propylene. Furthermore, industrial grade ethylene and propylene usually contains small amounts, for example up to about 10% by volume, ethane and propane, respectively. Therefore, since ethane and propane is not generally affected by ethylene and propylene partial oxidation catalysts, the effluent usually contains ethane or propane. In addition to these components the effluent will contain nitrogen and argon if air is used as oxidant.

In the past it was common to practice the above-described partial oxidation processes on a single-pass basis, with the conversion of hydrocarbon to the desired product being maximized. This resulted in low overall efficiency, since the selectivity to the desired partial oxidation product is below the maximum at high conversion. Consequently, the concentration of carbon oxides in the reactor effluent was high. The effluent stream was usually incinerated, so that the only return realized from the effluent was heat value from combustion of the hydrocarbon and carbon monoxide.

Later improvements included recycling part of the gaseous effluent to the reactor after recovery of the desired partial oxidation reaction product(s). This made it possible to lower hydrocarbon conversion and increase selectivity to the desired product. These improvements resulted in a reduced "per pass" conversion but the overall efficiency of the process was increased. However, in such recycle processes, part of the effluent remaining after recovery of the desired partial oxidation product(s) had to be purged from the system to prevent the build-up of carbon oxides and nitrogen and alkanes, such as ethane and propane.

Because of the difficulty of separating ethylene from ethane and propylene from propane efficient operation of recycle ethylene and propylene partial oxidation processes is hard to achieve when the alkene feed contains the corresponding alkane as an impurity. Poor separation of ethylene from ethane and propylene from propane in the post product recovery zone can result in a buildup of ethane or propane in the overall process. Continuous efforts are underway to enhance the efficiency of recycle partial oxidation processes. These efforts include investigations for improved procedures for separating the alkene from the corresponding alkane prior to recycling the alkene to the reactor. The present invention provides such an improved procedure.

SUMMARY OF THE INVENTION

The improvement of the present invention applies to a recycle process for producing ethylene and propylene partial oxidation products, such as ethylene oxide, ethylene dichloride, vinyl chloride, propylene oxide, acrylic acid and acrylonitrile, by the vapor phase oxidation of ethylene or propylene with oxygen in the presence of a suitable catalyst and any other necessary reactant, such as hydrogen chloride for ethylene dichloride and vinyl chloride production and ammonia for acrylonitrile production, recovering the partial oxidation product from the gaseous reactor effluent and recycling the unreacted alkene to the reaction zone.

According to one embodiment of the invention an ethylene stream which contains ethane as an impurity or propylene stream which contains propane as an impurity is subjected to a pressure swing adsorption (PSA) process or a temperature swing adsorption (TSA) process at an elevated temperature in one or more adsorption vessels containing an adsorbent which selectively adsorbs ethylene and propylene from gas mixtures containing one of these alkenes and one or more alkanes. The adsorption process is operated under conditions which result in the production of an adsorbed stream enriched in the alkene and a non-adsorbed product stream enriched in the corresponding alkane. The process is desirably operated to retain substantially all of the unreacted alkene in the adsorbed product gas stream and reject most of the alkane in the nonadsorbed waste stream. The alkene-enriched gas stream obtained upon desorption of the adsorption beds is contacted with an oxygen-containing gas and any other necessary reactants in the vapor phase in a reaction zone in the presence of an appropriate partial oxidation catalyst under conditions which cause partial oxidation of the alkene, thereby producing a gaseous product stream containing one or more partial oxidation products, byproduct carbon oxides, unreacted alkene and possibly some oxygen and other gaseous components, such as nitrogen. The gaseous product stream leaving the oxidation reactor is treated in a partial oxidation product recovery unit, such as a partial oxidation product condenser or a scrubber, in which substantially all of the partial oxidation product is recovered from the gas stream. The gas stream remaining after the partial oxidation recovery step can be discharged from the system and disposed of, but it is preferably introduced into a gas separation system wherein unreacted alkene is separated from the other gaseous components of the gas stream. The separated alkene is desirably recycled to the partial oxidation reactor.

In a preferred aspect of this embodiment of the invention the hot gaseous product stream leaving the partial oxidation reactor is cooled by indirect heat exchange with the alkene-alkane stream that is to be used as feed to the adsorption system, thereby heating the latter stream to the temperature at which the adsorption is to be carried out.

According to the preferred embodiment of the invention, an ethylene stream which contains ethane as an impurity or a propylene stream which contains propane as an impurity is first introduced into the above-described partial oxidation reactor, thereby producing a gaseous product stream containing one or more partial oxidation products, byproduct carbon oxides, unreacted alkene, some corresponding alkane and possibly excess oxygen and other gaseous components, such as nitrogen. The gaseous product stream leaving the oxidation reactor is treated in the partial oxidation product recovery unit to recover the desired partial oxidation product(s). After recovery of the partial oxidation product(s) from the gaseous product stream part or all of the partial oxidation product-free product stream is subjected to a pressure swing adsorption process or a temperature swing adsorption process at an elevated temperature in a bed of adsorbent which preferentially adsorbs alkenes from gas mixtures. The adsorption process is operated under conditions which result in the production of a non-adsorbed product stream containing substantially all of the oxygen and nitrogen and most of the carbon oxides and corresponding ethane or propane contained in the product stream, and an adsorbed component containing most of the unreacted ethylene or propylene and, usually, small amounts of carbon oxides and some ethane or propane. The process is desirably operated to retain substantially all of the unreacted alkene in the product gas stream and remove carbon dioxide, carbon monoxide and the corresponding alkane in excess of the amount that it is desired to maintain in the system as diluent.

In a preferred embodiment of the invention, the adsorbent is a type A zeolite, and in the most preferred embodiment, it is type 4A zeolite.

The adsorption step is typically carried out at a temperature in the range of about 0° C. to about 250° C., and is preferably carried out at a temperature above about 50° C. The preferred upper temperature limit is about 200° C. The adsorption step is most preferably carried out at a temperature in the range of about 70° to about 170° C. and an absolute pressure of about 1 to 20 bar.

The process of the invention is particularly useful for the production of ethylene oxide, vinyl chloride, ethylene dichloride, vinyl acetate, propylene oxide, acrolein, acrylic acid, propionic acid, i-propyl alcohol, acrylonitrile and mixtures of these.

In other preferred embodiments of the invention the partial oxidation reaction is carried out using substantially pure oxygen as the oxidant, the adsorption bed regeneration step is effected by vacuum means or by purging the bed with one or more of an inert gas, the non-adsorbed gas product from the adsorption system or the adsorbed product gas from the adsorption system, or by combinations of vacuum and purge regeneration; and bed repressurization is effected using the alkene-enriched desorbed gas from the adsorption system.

DETAILED DESCRIPTION OF THE INVENTION

As used in this specification, the term "alkene" means ethylene or propylene. When the alkene being referred to is ethylene the "corresponding alkane" is ethane and when the alkene is propylene the corresponding alkane is propane. The term "partial oxidation product", as used herein, means a chemical compound other than carbon monoxide and carbon dioxide produced by the oxidation of ethylene or propylene. Typical of the partial oxidation product manufacturing processes in which the invention can be employed are:

1. The manufacture of ethylene oxide by the reaction of ethylene with oxygen in the presence of a silver oxide catalyst supported on silica or alumina.
2. The manufacture of ethylene dichloride, and hence vinyl chloride, by the reaction of ethylene with oxygen and hydrogen chloride in the presence of a supported or unsupported catalyst such as mercuric chloride, ferric chloride, copper chloride, or potassium chloride.
3. The manufacture of propylene oxide by the reaction of propylene with oxygen in the presence of a silver oxide catalyst supported on silica or alumina or mixed molten nitrate salts. An example is the reaction of propylene with oxygen in the presence of molten sodium and potassium nitrate to produce propylene oxide.
4. The manufacture of acrolein by the reaction of propylene with oxygen over a molybdenum-bismuth-iron catalyst.
5. The manufacture of acrylonitrile by the reaction of propylene with oxygen and ammonia in the presence of a bismuth-molybdenum oxide catalyst or an iron-antimony oxide catalyst or uranium-antimony oxide supported on silica or alumina.

As is apparent from the above examples, the process of the invention can be used for the manufacture of various partial oxidation products by the reaction of ethylene or propylene with oxygen in the presence of an appropriate catalyst. The particular partial oxidation reaction that is carried out in the process of the invention is not critical to the invention. In general, the process of the invention can include any ethylene or propylene partial oxidation reaction that is carried out in the vapor phase at elevated temperatures to produce any partial oxidation product by the reaction of ethylene or propylene and oxygen (and, where appropriate, other reactants, such as ammonia, when the partial oxidation is ammoxidation) in the presence of a catalyst to produce the partial oxidation product as the main product and carbon dioxide and carbon monoxide as byproducts.

The invention can be better understood from the accompanying drawings in which the same reference numerals are used to designate the same or similar pieces of equipment in different figures. Auxiliary equipment, including compressors, heat exchangers and valves, not necessary for an understanding of the invention, have been omitted from the drawings to simplify discussion of the invention.

In a first embodiment of the invention an ethylene or a propylene feed stream containing the corresponding alkane as an impurity is purified to remove the alkane from the stream and the purified alkene stream is reacted in a partial oxidation reactor to produce the desired partial oxidation product. The gaseous product leaving the partial oxidation reactor is cooled and the partial oxidation product is separated from the cooled reactor effluent. Unreacted alkene remaining in the gas stream after product removal can be recovered from the gas stream and recycled to the partial oxidation reactor. This embodiment is illustrated in FIG. 1, in which purifier A is an adsorption system, B is a partial oxidation reactor, optional unit C is a heat exchanger, D is a product recovery unit and optional unit E is a gas separator.

Figure 1:
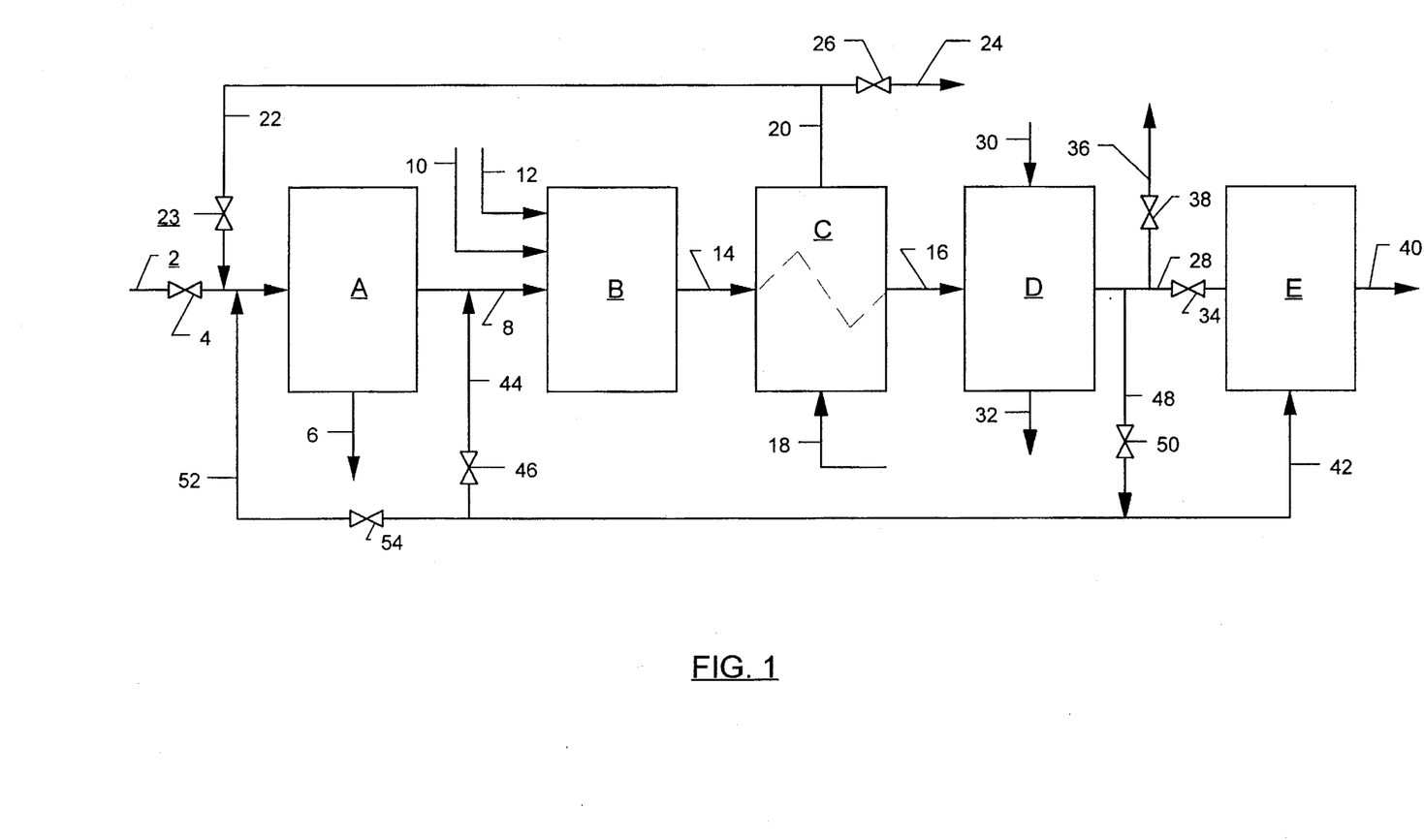
FIG. 1 illustrates, in a block diagram, one embodiment of a system for producing a partial oxidation product in accordance with the present invention.

Considering FIG. 1 in more detail, purifier A is a pressure swing or temperature swing adsorption system typically comprising two or more stationary beds packed with an adsorbent which preferentially adsorbs alkenes from a gas mixture containing an alkene and one or more alkanes. The beds are generally arranged in parallel and adapted to be operated in a cyclic process comprising adsorption and desorption. The cycle may contain steps other than the fundamental steps of adsorption and regeneration, and it is commonplace to have the system in which the adsorption is carried out comprise two or more adsorbent beds cycled out of phase to assure a pseudo-continuous flow of alkene-enriched gas from the outlet end of the adsorption system.

The adsorbent may be alumina, silica, zeolites, carbon molecular sieves, etc. Typical adsorbents include alumina, silica gel, carbon molecular sieves, zeolites, such as type A and type X zeolite, etc. The preferred adsorbents are type A zeolites, and the most preferred adsorbent is type 4A zeolite.

Type 4A zeolite, i.e. the sodium form of type A zeolite, has an apparent pore size of about 3.6 to 4 Angstrom units. This adsorbent provides enhanced selectivity and capacity in adsorbing ethylene from ethylene-ethane mixtures and propylene from propylene-propane mixtures at elevated temperatures. This adsorbent is most effective for use in the invention when it is substantially unmodified, i.e. when it has only sodium ions as its exchangeable cations. However, certain properties of the adsorbent, such as thermal and light stability, may be improved by partly exchanging some of the sodium ions with other cations. Accordingly, it is within the scope of the preferred embodiment of the invention to use a type 4A zeolite in which some of the sodium ions attached to the adsorbent are replaced with other metal ions, provided that the percentage of ions exchanged is not so great that the adsorbent loses its type 4A character. Among the properties that define type 4A character are the ability of the adsorbent to selectively adsorb ethylene from ethylene-ethane mixtures and propylene from propylene-propane gas mixtures at elevated temperatures, and to accomplish this result without causing significant oligomerization or polymerization of the alkenes present in the mixtures. In general, it has been determined that up to about 25 percent (on an equivalent basis) of the sodium ions in 4A zeolite can be replaced by ion exchange with other cations without divesting the adsorbent of its type 4A character. Cations that may be ion exchanged with the 4A zeolite used in the alkene-alkane separation include, among others, potassium, calcium, magnesium, strontium, zinc, cobalt, silver, copper, manganese, cadmium, aluminum, cerium, etc. When exchanging other cations for sodium ions it is preferred that less than about 10 percent of the sodium ions (on an equivalent basis) be replaced with such other cations. The replacement of sodium ions may modify the properties of the adsorbent. For example, substituting some of the sodium ions with other cations may improve the stability of the adsorbent.

Another class of preferred adsorbents are those which contain certain oxidizable metal cations, such as copper-containing adsorbents, which possess enhanced adsorptive capacity and selectivity with respect to the preferential adsorption of alkenes from gaseous alkene-alkane mixtures. Suitable adsorbent substrates for manufacturing copper-modified adsorbents include silica gel, and zeolite molecular sieves, such as zeolite type 4A, zeolite type 5A, zeolite type X and zeolite type Y. The manufacture and use of copper-modified adsorbents and examples of suitable copper-containing adsorbents are set forth in U.S. Pat. No. 4,917,711, the disclosure of which is incorporated herein by reference.

Purifier A is provided on its inlet end with alkene feed gas inlet line 2 which, in the embodiment illustrated in FIG. 1, is equipped with valve 4. On its outlet end purifier A is provided with alkane-enriched gas stream discharge line 6 and alkene-enriched gas line 8. Line 8 connects the outlet of purifier A to the inlet of reactor B.

Reactor B may be any suitable reactor and is preferably equipped with heat exchange means (not shown) to remove heat generated in the partial oxidation reaction, which is exothermic. In addition to alkene feed line 8, reactor B is provided on its inlet end with oxygen-containing gas feed line 1 0, and ammonia feed line 12, the latter being required only if acrylonitrile is to be produced. On its outlet end, reactor B is equipped with gaseous effluent line 14, which is connected to the inlet of heat exchanger C, if this unit is included in the system, or to the inlet of product recovery unit D, if heat exchanger is not used in the process.

In the embodiment illustrated in FIG. 1, heat exchanger C is provided with cooled gas outlet line 16 and with coolant inlet and outlet lines 18 and 20, respectively. Coolant outlet line 20 is, in turn, connected to the inlet end of purifier A via line 22, which is provided with valve 23, and to coolant discharge line 24, which is provided with valve 26. Line 16 connects the cooled gas outlet end of heat exchanger C to the gas inlet end of partial oxidation product recovery unit D.

Partial oxidation product recovery unit D can be any unit suitable for separating partial oxidation product from the reactor B gaseous effluent. Unit D is typically a condenser or a scrubber of the packed bed design equipped with means for spraying water or an aqueous or nonaqueous liquid on the product gas entering this unit from heat exchanger C (or from reactor B if the system does not include heat exchanger C). Unit D receives scrubbing liquid through inlet line 30 and discharges a liquid product containing substantially all of the partial oxidation product through partial oxidation product outlet line 32. In the embodiment illustrated in FIG. 1, unit D is also equipped with a partial oxidation product-free gas outlet line 28, which communicates with optional separator E through valve 34, waste gas discharge line 36, which is provided with valve 38 and recycle line 48, which is provided with valve 50.

The principal function of optional separator E is to remove byproduct carbon monoxide and carbon dioxide, and nitrogen, if present, from the gaseous effluent from product recovery unit D. Accordingly, separator E can be any device that will effect such separation. Separator E can be a single separator or a train of separators. In a preferred embodiment of the invention, separator E is a pressure swing adsorption system which contains an adsorbent which adsorbs the alkene or both the alkene and alkane in preference to the other components of the unit D gaseous effluent. Separator E is provided with waste gas discharge line 40, and alkene recycle line 42, which is connected to the inlet of partial oxidation reactor B through line 44 and to the inlet end of purifier A via line 52. Lines 42 and 52 are provided with valves 46 and 54, respectively.

According to the process of the invention practiced in the system of FIG. 1, an alkene feed gas stream which contains the corresponding alkane as an impurity and which is heated to the desired adsorption temperature is introduced into one or more of the adsorption vessels of purifier A. In one aspect of the FIG. 1 embodiment, the feed gas is heated externally of the system and introduced into the system through line 2 and valve 4 as a hot gas. In an alternative and preferred scheme, the alkene feed gas enters the system through line 18, is heated in heat exchanger C by heat exchange with hot reactor B effluent flowing through line 14, and flows through lines 20 and 22 and valve 23 and into purifier A.

The feed gas usually contains at least 90% by volume alkene, with the balance being substantially the corresponding alkane, and in preferred embodiments the concentration of alkene in the feed entering purifier A is at least about 95%. Purifier A is preferably operated in a manner which results in the adsorption of substantially all of the alkene in the feed gas. During the adsorption step most of the nonadsorbed alkane present is separated from the feed gas and discharged from the system as non-adsorbed gas through line 6.

The temperature at which the adsorption step is carried out depends upon a number of factors, such as the particular adsorbent being used, e.g. unmodified 4A zeolite, a particular metal-exchanged 4A zeolite or another adsorbent which selectively adsorbs alkenes from alkene-alkane mixtures, and the pressure at which the adsorption is carried out. In general, the adsorption step is carried out at a minimum temperature of about 0° C. and is preferably carried out at a minimum temperature of about 50° C. and is most preferably carried out at a temperature of at least about 70° C. The upper temperature limit at which the adsorption step in unit A is carried out is determined mostly by economics. In general the adsorption step can be carried out at a temperature below the temperature at which the alkene undergoes chemical reaction, such as polymerization. The upper adsorption temperature limit is about 250° C. When unmodified 4A zeolite is used as the adsorbent the reaction is generally carried out at or below 200° C., and is preferably carried out at a temperature at or below 170° C. When oxidizable metal containing adsorbents, particularly copper-containing adsorbents, are used as the adsorbent, the adsorption step can be most efficiently carried out at temperatures between about 100° C. and 250° C., and it is preferably carried out at temperatures in the range of about 125° to 200° C., and is most preferably carried out at temperatures in the range of about 150° to about 200° C.

The pressures at which the adsorption and regeneration steps of the unit A adsorption process are carried out are not critical, and in general, these steps can be carried out at any of the usual pressures employed for gas adsorption processes, with the limitation, of course, that the adsorption step be carried out at a pressure greater than the regeneration step pressure. Typically, when the adsorption process is pressure swing adsorption the absolute pressure during the adsorption step will range generally from about 0.2 to about 100 bar, and preferably from about 1 to 50 bar, and during the regeneration step will range from about 20 millibar to about 1 bar or more. When the adsorption process is temperature swing adoption the pressure during both adsorption and desorption is desirably atmospheric or near atmospheric.

When the adsorbed alkene front traveling through the vessel(s) of purifier A in which the adsorption step is being carried out reaches the desired point in the vessel(s), the adsorption process in these vessel(s) is terminated and these vessels enter the regeneration mode. During regeneration, the alkene-loaded vessels are depressurized, if the adsorption cycle is pressure swing adsorption, or heated, if a temperature swing adsorption cycle is employed. As the regeneration proceeds alkene-enriched gas is discharged from purifier A through line 8.

The alkene-enriched stream from purifier A next enters reactor B, where it mixes with oxygen-containing gas entering reactor B through line 10. If acrylonitrile is to be produced in reactor B, ammonia is introduced into the reactor through line 12. The various reactants may be separately introduced into reactor B or they may be combined and introduced into reactor B in a single line. The particular inlet arrangement will generally depend upon the type of reactor used for practicing the invention. In fixed bed reactor systems the components of the feed are often mixed before they enter the reactor and are thus fed into the reactor through a single line, whereas in fluidized bed reactor systems, the components are often separately fed into the reactor.

The oxygen-containing gas can be air, oxygen-enriched air, other oxygen-inert gas mixtures or substantially pure oxygen. By oxygen-enriched air is meant air that contains more oxygen than is naturally present in air. Oxygen-inert gas mixtures include oxygen-nitrogen mixtures, oxygen-argon mixtures, oxygen-carbon dioxide mixtures, etc. substantially pure oxygen is preferred since its use avoids the introduction of substantial amounts of inert gases such as nitrogen and argon into the system and the subsequent need to remove excess quantities of these inert gases from the product gas stream to prevent their buildup in the system. Substantially pure oxygen is defined for this specification as a gas stream containing at least 98% by volume oxygen.

In reactor B, the gas mixture contacts the catalyst at the conventional conditions of temperature and pressure specified below and reacts to form the product gases. Any of the well-known catalysts for oxidizing alkene to the desired partial oxidation product under the specified conditions can be used in the process of the invention. In the case of ethylene partial oxidation suitable catalysts include silver oxide supported on silica or alumina or mixtures thereof, and in the case of propylene partial oxidation suitable catalysts include bismuth molybdate for the first stage and a mixed molybdenum-tungsten- vanadium catalyst for the second stage of a two-stage process for the preparation of acrylic acid from propylene; silver oxide or mixed molten nitrates for the preparation of propylene oxide; and multi-component molybdate catalysts or antimony-containing catalysts for the preparation of acrylonitrile. These catalysts and their use are conventional and well known to those skilled in the manufacture of partial oxidation products, and the specific partial oxidation catalysts used in the process do not form a critical part of the invention.

The conditions of the partial oxidation reaction are well known and likewise form no part of the invention. Typically, the oxidation reaction is conducted at a temperature in the range of about 120° to about 600° C., and usually in the range of about 150° to about 500° C., and at pressures typically in the range of about 1.1 to about 40 bar, and usually in the range of about 1.2 to about 25 bar. The reactants are generally passed through the reactor at a velocity in the range of about 0.1 to about 5.0 ft/sec. The volume ratio of oxygen to hydrocarbon in the feed is suitably in the range of about 0.3:1 to about 50:1.

The partial oxidation reaction is highly exothermic; accordingly a considerable quantity of heat is generated in reactor B and a hot gaseous effluent is discharged from this reactor through line 14. The hot effluent is desirably cooled by passage through heat exchanger C. As noted above, the hot gaseous effluent is cooled by indirect heat exchange with propylene feed gas entering the system through line 18. Alternatively, the hot effluent can be cooled by indirect heat exchange with a fluid other than the feed gas, such as water. During the cooling some partial oxidation product may condense. The condensed product can be separated from the gas effluent in heat exchanger C and later combined with the product recovered in product recovery unit D, or if desired, all of the partially condensed gas mixture can be sent to product recovery unit D for separation from the remaining components of the reactor effluent.

The product gas stream leaving reactor B contains the desired partial oxidation product as the main product, and carbon dioxide and carbon monoxide as by-products. As noted above, the product stream generally also contains unreacted alkene and oxygen, and may contain small amounts of other by-products, impurity gases and the corresponding alkane. The product gas stream leaves reactor B via line 14 and next passes through heat exchanger C (if included in the system) wherein it is cooled generally to a temperature in the range of about 30° to about 200° C. The cooled product gas stream then enters partial oxidation product removal means D, in which the partial oxidation product is removed from the gas stream. Some partial oxidation products condense from the reactor effluent stream upon cooling, others are best removed by means of a scrubber. When partial oxidation product removal means 8 is a scrubber, the product gases are intimately contacted with a solvent for the partial oxidation product. The solvent, which is often water, dissolves substantially all of the partial oxidation product in the product gas stream and the partial oxidation product-containing solution exits scrubber D via line 32. It is usually further treated to recover the partial oxidation product. The scrubbed gas stream leaves partial oxidation product removal means D through line 28. In one aspect of this embodiment the scrubbed gas stream enters separator E through valve 34. In this aspect valves 38 and 50 are closed.

Separator E is preferably operated in a manner which rejects from the system carbon dioxide in excess of the amounts which it is desired to recycle. When the system is operated for a period of time equilibrium is reached, after which a quantity of carbon oxides approximately equal to the quantity produced in the oxidation step in each pass is removed from the system by separator E. Other inert gases, such as nitrogen and argon (introduced into the system when air is used as the source of oxygen) are also removed from the system by means of separator E. To prevent the buildup of nitrogen and argon in the system when air used as the source of oxygen, it is generally preferred to remove from the system substantially all of the nitrogen and argon entering reactor B.

Rejected gases exit separator E through line 40 and are discharged from the system for further treatment or disposal. Unreacted alkene leaves separator E through line 42 and it is recycled to either purifier A or reactor B. When the alkane content of the gas stream flowing through line 42 is low it is preferable to recycle at least part of this stream directly to reactor B. This is accomplished by opening valve 46. On the other hand, if the stream in line 42 contains a significant concentration of alkane it is preferable to recycle all of this stream to purifier A so that the alkane can be removed. This is accomplished by opening valve 54 and closing valve 46.

In some cases it may be preferable to have part or all of the gas stream leaving partial oxidation product recovery unit means D bypass separator E and be recycled directly to purifier A. This can be effected by opening valve 50 and closing or leaving open valve 34. This alternative is advantageous when it is desired to use purifier A to remove all gases other than the alkene reactant from the system.

In a further aspect, the system of FIG. 1 can be operated as a single pass system. In this aspect valves 34 and 50 are closed and valve 38 is opened and the components of the unit D gaseous effluent are discharged from the system through line 36 for further processing or disposal.

Figure 2:
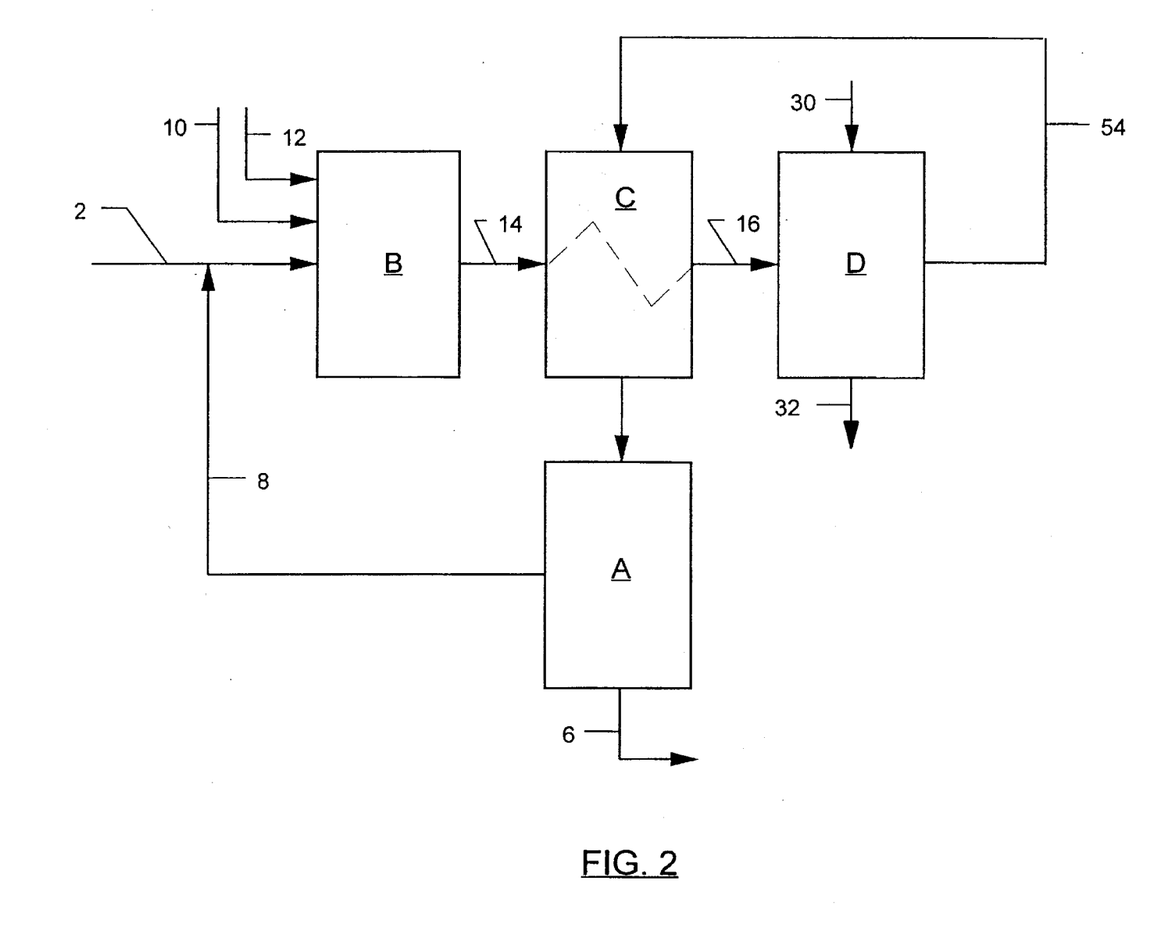
FIG. 2 illustrates, in a block diagram, an alternate embodiment of the system illustrated in FIG. 1.

The system illustrated in FIG. 2 is a variation of the system of FIG. 1. Units A, B, C and D of FIG. 2 are identical to or similar to the corresponding units of FIG. 1. As was the case with the FIG. 1 system, heat exchanger C is optional in the system of FIG. 2. The principal difference between the system of FIGS. 1 and 2 is that in the FIG. 2 system purifier A is positioned downstream of reactor B. In this arrangement the alkene feed entering the system flows directly to reactor B. In the FIG. 2 system the oxidant and ammonia (if used) are introduced into reactor B through lines 10 and 12, respectively, as in the FIG. 1 system.

In the process of the invention as practiced in the system of FIG. 2, the gaseous effluent from partial oxidation product recovery means D passes through line 54 and enters heat exchanger C, wherein it is heated by indirect heat exchange with the reactor B effluent to the temperature at which the adsorption in purifier A is to carried out. In the exchange the hot reactor B gaseous effluent is cooled to the temperature at which the scrubbing process in unit D is to be conducted. In the system of FIG. 2, the alkene-enriched stream leaving purifier A passes through line 8 and is recycled to reactor B. In this system purifier A serves to remove not only alkane but also carbon oxides and other gases from the recycle stream. The system of FIG. 2 is preferred for use when the alkene feed gas contains relatively small concentrations of the corresponding alkane, for example concentrations of less than about 10% by volume.

As was the case in the FIG. 1 system, it is not necessary in the FIG. 2 system that the gaseous effluent from product recovery unit D be heated by passage through heat exchanger C. If desired, this stream can be heated by an external source of heat. This would be the case if heat exchanger C were not included in the FIG. 2 system.

It will be appreciated that it is within the scope of the present invention to utilize conventional equipment to monitor and automatically regulate the flow of gases within the system so that it can be fully automated to run continuously in an efficient manner.

An important advantage of the invention is that it permits the process of this invention to be run at a relatively low per pass conversion of the alkene feed to the desired product to achieve substantially improved selectivity. It will be appreciated that a system that achieves enhanced selectivity, and hence increased overall yield of a desired product, is highly beneficial.

The invention is further illustrated by the following example in which, unless otherwise indicated, parts, percentages and ratios are on a volume basis.

EXAMPLE I

This hypothetical example depicts a vapor phase acrylonitrile production run using as feed components propylene containing 93% propylene and 7% propane, air and ammonia. The example is simulated for a reaction system similar to the system of FIG. 2. The simulated feed to the partial oxidation reactor (stream 2) is comprised of the fresh feed component (stream 1) and the recycle component (stream 5). The partial oxidation reactor effluent (stream 3) exits the reactor at a temperature of about 450° C., is cooled by heat exchange with the effluent from the product scrubber (stream 4) and enters the scrubber for acrylonitrile recovery. After being heated to about 100° C. in the heat exchanger, the scrubber effluent enters the pressure swing adsorption system. The adsorption process is carried out at an adsorption pressure of 0.7 bar and a bed regeneration pressure of 300 mbar. The recycle stream (stream 5) contains most of the propylene contained in the feed to the adsorption unit and the waste gas stream (stream 6) contains most of the propane, nitrogen, oxygen and carbon oxide byproducts entering the adsorption unit. The flow rates and stream analyses are recorded in Table I.

TABLE I

| | | STREAM | | | | | | | | | | | |
|---|---|---|---|---|---|---|---|---|---|---|---|---|---|
| | | 1 | | 2 | | 3 | | 4 | | 5 | | 6 | |
| Comp. | Select. | kg-mol/hr | % | kg-mol/hr | % | kg-mol/hr | % | kg-mol/hr | % | kg-mol/hr | % | kg-mol/hr | % |
| $C_3H_6$ | | 302.1 | 6.8 | 313.4 | 6.49 | 12.5 | 0.3 | 12.54 | 0.34 | 11.3 | 2.9 | 1.3 | 0.0 |
| $O_2$ | | 792.1 | 17.8 | 793.7 | 16.4 | 174.7 | 3.5 | 174.70 | 4.72 | 8.7 | 2.3 | 166.0 | 5.0 |
| $N_2$ | | 2989.6 | 67.1 | 3146.9 | 65.2 | 3146.9 | 62.8 | 3146.93 | 84.94 | 157.3 | 41.1 | 2986.6 | 90.0 |
| $C_3H_8$ | | 23.6 | 0.5 | 29.1 | 0.6 | 29.1 | 0.6 | 29.12 | 0.79 | 5.5 | 1.4 | 23.6 | 0.7 |
| $NH_3$ | | 344.7 | 7.7 | 344.7 | 7.14 | 52.5 | 1.0 | | | | | | |
| AN[1] | 77.0 | | 0.0 | | 0.0 | 231.7 | 4.6 | | | | | | |
| HCN | 6.5 | | 0.0 | | 0.0 | 58.7 | 1.2 | | | | | | |
| ACR[2] | 0.4 | | 0.0 | | 0.0 | 1.3 | 0.0 | | | | | | |
| ACN[3] | 0.4 | | 0.0 | | 0.0 | 1.9 | 0.0 | | | | | | |
| CO | 2.7 | | 0.0 | 1.3 | 0.0 | 25.7 | 0.5 | 25.73 | 0.69 | 1.3 | 0.3 | 24.4 | 0.7 |
| $CO_2$ | 13.0 | | 0.0 | 29.4 | 0.6 | 147.1 | 2.9 | 147.12 | 3.97 | 29.4 | 7.7 | 117.7 | 3.5 |
| $H_2O$ | | | 0.0 | 169.0 | 3.5 | 1128.4 | 22.5 | 168.75 | 4.56 | 169.0 | 44.2 | 0.0 | 0.0 |
| TOTAL | 0.0 | 4452.1 | 100.0 | 4827.5 | 100.0 | 5010.5 | 100.0 | 3705.08 | 100.0 | 382.56 | 100.00 | 3322.5 | 100.0 |

[1] Acrylonitrile
[2] Acrolein
[3] Acetonitrile

EXAMPLE II

This hypothetical example depicts a vapor phase propylene oxide production run using as feed components propylene containing 98% propylene and 2% propane and oxygen. The example is simulated for a reaction system similar to the system of FIG. 2. The simulated feed to the partial oxidation reactor (stream 2) is comprised of the fresh feed component (stream 1) and the recycle component (stream 5). The partial oxidation reactor effluent (stream 3) exits the reactor at a temperature of about 400° C., is cooled by heat exchange with the effluent from the product scrubber (stream 4) and enters the scrubber for propylene oxide recovery. After being heated to about 100° C. in the heat exchanger, the scrubber effluent enters the pressure swing adsorption system. The adsorption process is carried out at an adsorption pressure of 0.7 bar and a bed regeneration pressure of 300 mbar. The recycle stream (stream 5) contains most of the propylene contained in the feed to the adsorption unit and the waste gas stream (stream 6) contains most of the propane, oxygen and carbon oxide byproducts entering the adsorption unit. The flow rates and stream analyses are recorded in Table II.

Although the invention has been described with particular reference to specific examples, variations are contemplated. For example, the reaction can be carried out under conditions that will effect the production of other partial oxidation products. Similarly, other catalysts and adsorbents and other means of gas separation can be used in the invention, if desired. Similarly, the process of the invention may be practiced in equipment arrangements other than those illustrated in the drawings. The scope of the invention is limited only by the breadth of the appended claims.

We claim:

1. A process for the production of a partial oxidation product comprising the steps:

(a) selectively adsorbing propylene from a propylene-propane gas mixture by passing said gas mixture through an adsorption zone containing an adsorbent which selectively adsorbs propylene;

(b) regenerating said adsorbent, thereby producing propylene-enriched gas;

(c) contacting said propylene-enriched gas with an oxygen-containing gas in a reaction zone in the presence of an appropriate oxidation catalyst under conditions

TABLE II

| | | STREAM | | | | | | | | | | | |
|---|---|---|---|---|---|---|---|---|---|---|---|---|---|
| | | 1 | | 2 | | 3 | | 4 | | 5 | | 6 | |
| Comp. | Select. | moles | % | moles | % | moles | % | moles | % | moles | % | moles | % |
| $C_3H_6$ | | 200.0 | 51.2 | 714.3 | 77.0 | 571.4 | 64.6 | 571.4 | 83.3 | 514.3 | 95.6 | 57.1 | 38.5 |
| $C_3H_8$ | | 4.1 | 1.0 | 5.8 | 0.6 | 5.8 | 0.7 | 5.8 | 0.8 | 1.7 | 0.3 | 4.1 | 2.8 |
| $O_2$ | | 186.3 | 47.7 | 189.8 | 20.5 | 17.7 | 2.0 | 17.7 | 2.6 | 3.5 | 0.7 | 14.2 | 9.5 |
| PO | 70.0 | | | | | 100.0 | 11.3 | | | | | | |
| ACETONE | 6.0 | | | | | 8.6 | 1.0 | | | | | | |
| ACOH | 3.0 | | | | | 4.3 | 0.5 | | | | | | |
| HCHO | 2.0 | | | | | 8.6 | 1.0 | | | | | | |
| $CH_3CHO$ | 2.0 | | | | | 4.3 | 0.5 | | | | | | |
| CO | 2.0 | | | 2.1 | 0.2 | 10.7 | 1.2 | 10.7 | 1.6 | 2.1 | 0.4 | 8.6 | 5.8 |
| $CO_2$ | 15.0 | | | 16.1 | 1.7 | 80.4 | 9.1 | 80.4 | 11.7 | 16.1 | 3.0 | 64.3 | 43.4 |
| $H_2O$ | | | | | | 72.9 | 8.2 | | | | | | |
| TOTAL | 100.0 | 390.4 | 100.0 | 928.2 | 100.0 | 884.6 | 100.0 | 686.0 | 100.0 | 537.8 | 100.0 | 148.2 | 100.0 | which result in the production of a gaseous product containing the desired partial oxidation product; and (d) recovering said partial oxidation product from the gaseous product.

2. The process of claim 1 further comprising recycling at least part of the gaseous product remaining after step (d) to said adsorption zone or to said reaction zone or to both said adsorption zone and said reaction zone.

3. The process of claim 1, further comprising passing at least part of the gaseous product remaining after step (d) through a gas separation zone, thereby separating a propylene-propane stream from said gaseous product, and recycling the separated propylene-propane stream to said adsorption zone or said reaction zone.

4. The process of claim 1 further comprising heating said gas mixture prior to passing said gas mixture through said adsorption zone by heat exchanging said gas mixture with the gaseous product from said reaction zone.

5. A process for the production of a partial oxidation product comprising the steps:

(a) contacting a propylene-propane mixture and an oxygen-containing gas with a partial oxidation catalyst in a reaction zone under conditions which result in the production of a gaseous product containing said partial oxidation product, unreacted propylene and propane;

(b) recovering said partial oxidation product from said gaseous product;

(c) selectively adsorbing propylene from said gaseous product by passing said gaseous product through an adsorption zone containing an adsorbent which selectively adsorbs propylene;

(d) regenerating said adsorbent, thereby producing a propylene-enriched gas stream; and (e) recycling said propylene-enriched gas stream to said reaction zone.

6. The process of claim 5 further comprising cooling the gaseous product produced in step (a) by heat exchanging said gaseous product with said propylene-enriched gas stream prior to passing said gaseous product through said adsorption zone.

7. The process of claim 1 or claim 5, wherein the adsorption step is conducted at a temperature above about 50° C.

8. The process of claim 7, wherein the adsorption step is conducted at a temperature in the range of about 50° to about 250° C.

9. The process of claim 8, wherein the adsorbent is selected from alumina, type 4A zeolite, type 5A zeolite, type 13X zeolite, type Y and mixtures of these.

10. The process of claim 9, wherein said adsorbent is type 4A zeolite.

11. The process of claim 10, wherein said adsorbent contains exchangeable cations other than sodium ions, but at a level insufficient to divest the adsorbent of its type 4A character.

12. The process of claim 10, wherein the adsorption step is carried out at a temperature in the range of about 50° to about 200° C. and an absolute pressure in the range of about 0.2 to 100 bar.

13. The process of claim 12, wherein said oxygen-containing gas is substantially pure oxygen.

14. The process of claim 13, wherein the adsorption step is carried out at a temperature in the range of about 70° to about 170° C. and an absolute pressure of about 1 to 50 bar.

15. The process of claim 14, wherein said partial oxidation product is selected from propylene oxide, acrolein, acrylic acid, propionic acid, i-propyl alcohol, acrylonitrile and mixtures of these.

16. A process for the production of a partial oxidation product comprising the steps:

(a) contacting a propylene-propane mixture containing at least 90% propylene and an oxygen-containing gas with a partial oxidation catalyst in a reaction zone under conditions which result in the production of a gaseous product containing said partial oxidation product, unreacted propylene and propane;

(b) cooling said gaseous product by heat exchanging said gaseous product with the gas stream from step (c), thereby heating said gas stream;

(c) recovering said partial oxidation product from the cooled gaseous product, thereby yielding a gas stream substantially free of partial oxidation product;

(d) selectively adsorbing propylene from the heated gas stream by passing said heated gas stream through a bed of adsorbent which selectively adsorbs propylene at a temperature in the range of about 50° to about 200° C. and an absolute pressure in the range of about 0.2 to about 20 bar;

(e) regenerating said bed of adsorbent, thereby producing a propylene-enriched gas stream; and (f) recycling said propylene-enriched gas stream to said reaction zone.

17. A process for the production of a partial oxidation product comprising the steps:

(a) selectively adsorbing propylene from a heated propylene-propane feed gas mixture by passing said feed gas mixture through a bed of adsorbent which selectively adsorbs propylene at a temperature in the range of about 50° to about 200° C.;

(b) regenerating said bed of adsorbent, thereby producing a propylene-enriched gas;

(c) contacting said propylene-enriched gas with an oxygen-containing gas in a reaction zone in the presence of an appropriate oxidation catalyst under conditions which result in the production of a hot gaseous product containing the desired partial oxidation product;

(d) cooling said hot gaseous product by indirectly heat exchanging said hot gaseous product with a propylene-propane gas mixture, thereby providing the heated feed gas mixture processed in step (a); and (e) recovering said partial oxidation product from the cooled gaseous product.

18. A process for the production of a partial oxidation product comprising the steps:

(a) selectively adsorbing ethylene from an ethylene-ethane gas mixture by passing said gas mixture through an adsorption zone containing an adsorbent which selectively adsorbs ethylene;

(b) regenerating said adsorbent, thereby producing ethylene-enriched gas;

(c) contacting said ethylene-enriched gas with an oxygen-containing gas in a reaction zone in the presence of an appropriate oxidation catalyst under conditions which result in the production of a gaseous product containing the desired partial oxidation product; and (d) recovering said partial oxidation product from the gaseous product.

19. The process of claim 18 further comprising recycling at least part of the gaseous product remaining after step (d) to said adsorption zone, to said reaction zone or to both said adsorption zone and said reaction zone.

20. The process of claim 18, further comprising passing at least part of the gaseous product remaining after step (d) through a gas separation zone, thereby separating an ethylene-ethane stream from said gaseous product, and recycling the separated ethylene-ethane stream to said adsorption zone or said reaction zone.

21. The process of claim 18 further comprising heating said gas mixture prior to passing said gas mixture through said adsorption zone by heat exchanging said gas mixture with the gaseous product from said reaction zone.

22. A process for the production of a partial oxidation product comprising the steps:
(a) contacting an ethylene-ethane mixture and an oxygen-containing gas with a partial oxidation catalyst in a reaction zone under conditions which result in the production of a gaseous product containing said partial oxidation product, unreacted ethylene and ethane;
(b) recovering said partial oxidation product from said gaseous product;
(c) selectively adsorbing ethylene from said gaseous product by passing said gaseous product through an adsorption zone containing an adsorbent which selectively adsorbs ethylene;
(d) regenerating said adsorbent, thereby producing an ethylene-enriched gas stream; and
(e) recycling said ethylene-enriched gas stream to said reaction zone.

23. The process of claim 22 further comprising cooling the gaseous product produced in step (a) by heat exchanging said gaseous product with said ethylene-enriched gas stream prior to passing said gaseous product through said adsorption zone.

24. The process of claim 18 or claim 22, wherein the adsorption step is conducted at a temperature above about 50° C.

25. The process of claim 24, wherein the adsorption step is conducted at a temperature in the range of about 50° to about 250° C.

26. The process of claim 25, wherein the adsorbent is selected from alumina, type 4A zeolite, type 5A zeolite, type 13X zeolite, type Y zeolite and mixtures of these.

27. The process of claim 26, wherein said adsorbent is type 4A zeolite.

28. The process of claim 27, wherein said adsorbent contains exchangeable cations other than sodium ions, but at a level insufficient to divest the adsorbent of its type 4A character.

29. The process of claim 27, wherein the adsorption step is carried out at a temperature in the range of about 50° to about 200° C. and an absolute pressure in the range of about 0.2 to 100 bar.

30. The process of claim 29, wherein said oxygen-containing gas is substantially pure oxygen.

31. The process of claim 30, wherein the adsorption step is carried out at a temperature in the range of about 70° to about 170° C. and an absolute pressure of about 1 to 50 bar.

32. The process of claim 30 wherein said zeolite type 4A contains copper ions and the adsorption step is carried out at a temperature in the range of about 100° to about 200° C. and an absolute pressure of about 1 to 50 bar.

33. The process of claim 30, wherein said partial oxidation product is selected from ethylene oxide, ethylene dichloride, vinyl chloride vinyl acetate and mixtures of these.

34. The process of claim 33 wherein said adsorption step is carried out at a temperature in the range of about 150° to about 200° C.

35. A process for the production of a partial oxidation product comprising the steps:
(a) contacting an ethylene-ethane mixture containing at least 90% ethylene and an oxygen-containing gas with a partial oxidation catalyst in a reaction zone under conditions which result in the production of a gaseous product containing said partial oxidation product, unreacted ethylene and ethane;
(b) cooling said gaseous product by heat exchanging said gaseous product with the gas stream from step (c), thereby heating said gas stream;
(c) recovering said partial oxidation product from the cooled gaseous product, thereby yielding a gas stream substantially free of partial oxidation product;
(d) selectively adsorbing ethylene from the heated gas stream by passing said heated gas stream through an adsorbent which selectively adsorbs ethylene at a temperature in the range of about 50° to about 200° C. and an absolute pressure in the range of about 0.2 to about 20 bar;
(e) regenerating said bed of adsorbent, thereby producing an ethylene-enriched gas stream; and
(f) recycling said ethylene-enriched gas stream to said reaction zone.

36. A process for the production of a partial oxidation product comprising the steps:
(a) selectively adsorbing ethylene from a heated ethylene-ethane feed gas mixture by passing said feed gas mixture through a bed of adsorbent which selectively adsorbs ethylene at a temperature in the range of about 50° to about 200° C.;
(b) regenerating said bed of adsorbent, thereby producing ethylene-enriched gas;
(c) contacting said ethylene-enriched gas with an oxygen-containing gas in a reaction zone in the presence of an appropriate oxidation catalyst under conditions which result in the production of a hot gaseous product containing the desired partial oxidation product;
(d) cooling said hot gaseous product by indirectly heat exchanging said hot gaseous product with an ethylene-ethane gas mixture, thereby providing the heated feed gas mixture processed in step (a); and
(e) recovering said partial oxidation product from the cooled gaseous product.

37. The process of any one of claims 1, 5, 16, 17, 18, 22, 35 or 36, wherein the adsorption and regeneration steps comprise a pressure swing adsorption cycle.

38. The process of any one of claims 1, 5, 16, 17, 18, 22, 35 or 36, wherein the adsorbent contains an oxidizable metal.

39. The process of claim 38, wherein said oxidizable metal is copper.

40. The process of claim 39, wherein the adsorption step is carried out at a temperature in the range of about 50° to about 250° C.

41. The process of claim 39, wherein the adsorption step is carried out at a temperature between 100° and 200° C.

* * * * *